United States Patent [19]

Katoh et al.

[11] Patent Number: 5,236,924

[45] Date of Patent: Aug. 17, 1993

[54] PYRIMIDINE DERIVATIVES AND FUNGICIDES AND/OR ACARICIDES CONTAINING THEM AS ACTIVE INGREDIENT

[75] Inventors: Tsuguihiro Katoh; Hirotaka Takano, both of Hyogo; Hiroaki Fujimoto, Osaka; Hirosi Kisida, Hyogo, all of Japan

[73] Assignee: Sumitomo Chemical Co., Ltd., Osaka, Japan

[21] Appl. No.: 906,437

[22] Filed: Jun. 30, 1992

Related U.S. Application Data

[63] Continuation-in-part of Ser. No. 732,007, Jul. 18, 1991, abandoned.

[30] Foreign Application Priority Data

Jul. 18, 1990 [JP] Japan ................................. 2-191346
May 31, 1991 [JP] Japan ................................. 3-157833

[51] Int. Cl.$^5$ .................... A01N 43/54; C07D 239/70
[52] U.S. Cl. ........................................ 514/258; 544/253
[58] Field of Search ..................... 514/258; 544/253

[56] References Cited

FOREIGN PATENT DOCUMENTS 0057440 8/1982 European Pat. Off. .
0128648 12/1984 European Pat. Off. .
0196524 10/1986 European Pat. Off. .
0276406 8/1988 European Pat. Off. .
0331529 9/1989 European Pat. Off. .
0453137 10/1991 European Pat. Off. .
2824768 12/1978 Fed. Rep. of Germany .
2036025 6/1980 United Kingdom .

OTHER PUBLICATIONS

Patent Abstracts of Japan, vol. 8, No. 126 (C228)[1563], Jun. 13, 1984.

*Primary Examiner*—John M. Ford
*Attorney, Agent, or Firm*—Sughrue, Mion, Zinn, Macpeak & Seas

[57] ABSTRACT

A compound which is effective as an active ingredient of fungicides and/or acaricides, and is represented by the formula and a method for preparing the same are provided:

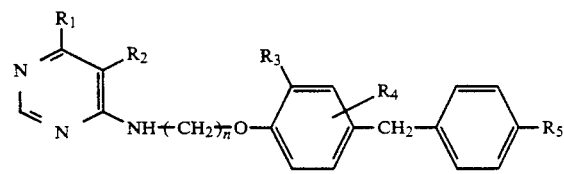

wherein $R_1$ and $R_2$ are bonded together at their termini and represent trimethylene or teramethylene, $R_3$ represents a hydrogen atom, a lower alkyl group or a halogen atom, $R_4$ represents a hydrogen atom or a lower alkyl group, $R_5$ represents a hydrogen atom, a lower alkyl group or a methylthio group and n represents 2 or 3.

14 Claims, No Drawings

PYRIMIDINE DERIVATIVES AND FUNGICIDES AND/OR ACARICIDES CONTAINING THEM AS ACTIVE INGREDIENT

This is a continuation-in-part of U.S. Ser. No. 07/732,007 filed Jul. 18, 1991.

The present invention relates to pyrimidine derivatives and fungicides and/or acaricides which contain them as an active ingredient.

Japanese Patent Kokai Nos. 63-156781 and 55-76804, etc. disclose that some of pyrimidine derivatives have fungicidal and/or acaricidal activities. However, activities of these compounds as fungicides and/or acaricides are not necessarily satisfactory.

Under the circumstances, the inventors have conducted intensive research and have found that the pyrimidine derivatives represented by the following formula (I) have excellent fungicidal, and/or acaricidal activities. As a result, the present invention has been accomplished.

That is, the present invention provides pyrimidine derivatives (hereinafter referred to as "the present compounds") represented by the formula:

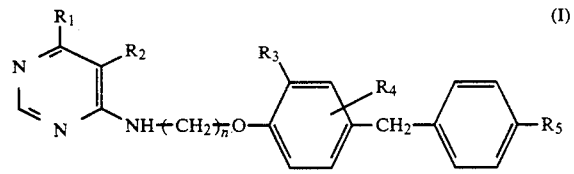

wherein $R_1$ and $R_2$ are bonded together at their termini and represent a trimethylene group or a tetramethylene group, $R_3$ represents a hydrogen atom, a lower alkyl group or a halogen atom, $R_4$ represents a hydrogen atom or a lower alkyl group, $R_5$ represents a hydrogen atom, a lower alkyl group or a methylthio group, and n represents 2 or 3, a method for producing them, and fungicides, insecticides and/or acaricides containing them as an active ingredient.

In the above formula (I), the lower alkyl group includes alkyl groups of 1–4 carbon atoms such as, for example, methyl group, ethyl group, n-propyl group, isopropyl group, and n-butyl group.

The halogen atom includes fluorine atom, chlorine atom, bromine atom and iodine atom.

With reference to the substituents in the formula (I). the following can be mentioned from the points of fungicidal and/or acaricidal activities, etc.

Among the present compounds, preferred are those which are represented by the formula (I) where $R_1$ and $R_2$ are bonded together at their terminals to form a trimethylene group or a tetramethylene group and where $R_3$, $R_4$ and $R_5$ each represents a hydrogen atom, or $R_3$ and $R_4$ each represents a hydrogen atom and $R_5$ represents a methyl group or a methylthio group, or $R_3$ represents a methyl group and $R_4$ and $R_5$ each represents a hydrogen atom, or $R_3$ and $R_4$ each represents a hydrogen atom and $R_5$ represents a hydrogen atom or a methyl group. So far as $R_3$, $R_4$ and $R_5$ are concerned, preferred one is a compound wherein $R_3$ is a methyl group and $R_4$ and $R_5$ each is a hydrogen atom. A compound wherein $R_3$ and $R_4$ each is a methyl group and $R_5$ is a hydrogen atom or a methyl group is preferred as acaricides. The suffix "n" is preferably 2.

The present compounds exhibit controlling effects in preventive, curative and systemic controlling effects against various plant diseases. The following are plant diseases against which the present compound has a controlling effect.

*Pyricularia oryzae, Cochliobolus miyabeanus* and *Rhizoctonia solani* of rice; *Erysiphe graminis,* f. SP. *hordei, f.* SP. *tritici, Gibberella zeae, Puccinia striiformis, P. graminis, P. recodita, P. hordei, Typhula sp., Micronectriella nivalis, Ustilago tritici, U. nuda, Tilletia caries, Pseudocercosporella herpotrichoides, Rhynchosporium secalis, Septoria tritici* and *Leptosphaeria nodorum* of wheat; *Diaporthe citri, Elsinoe fawcetti, Penicillium digitatum* and *P. italicum* of citrus fruits; *Sclerotinica mail, Valsa mail, Podpsphaera leucotricha, Alternaria mail* and *Venturia inaequalis* of apple; *Venturia nashicola, V. pirina, Alternaria kikuchiana* and *Gymnosporangium haraeanum* of Pear; *Sclerotinia cinerea, Cladosporium carpophilum* and *Phomopsis sp.* of peach; *Elsinoe ampelina, Glomerella cingulata, Uncinula necator, Phakopsora ampelopsidis, Guignardia bidwellii* and *Plasmopara viticola* of grape; *Gloeosprorium kaki, Cercospora kaki* and *Mycosphaerella nawae* of persimmon; *Colletotrichum lagenarium, Sphaerotheca fuliginea, Mycosphaerella melonis, Pseudoperonospora cubensis* and *Phytophthora sp.* of cucumber; *Alternaria solani, Cladosporium fulvum* and *Phytophthora infestans* of tomato; *Phomopsis vexans* and *Erysiphe cichoracearum* of eggplant; *Alternaia japonica* and *Cercosporella brassicae* of rape vegetable; *Puccinia allii* of Welsh onion; *Cercospora kikuchii, Elsinoe glycines* and *Diaporthe phaseolorum var. sojae* of soybean; *Colletotrichum lindemthianum* of kidney bean; *Mycosphaerella personatum* and *Cercospora arachidicola* of peanut; *Erysiphe pisi* of pean; *Alternaria solani* and *Phytophthora infestans* of potato; *Sphaerotheca humuli* of strawberry; *Exobasidium reticulatum* and *Elsinoe leucospila* of tea plant; *Alternaria longipes, Erysiphe cichoracearum, Colletotrichum tabacum, Peronospora tabacina* and *Phyrophthora nicotianae* of tabacco; *Cercospora beticola* of beet; *Diplocarpon rosae* and *Sphaerotheca pannosa* of rose; *Septoria chrysanthemi-indici* and *Puccinia horiana* of chrysanthemum; and *Botrytis cinerea* and *Sclerotinia sclerotiorum* of various crops.

Among them, the present compounds are especially effective against downy mildew and late blight of various plants.

The following are harmful acarines against which the present compounds are effective.

Spider mites

Carmine spider mite, twospotted spider mite, Kanzawa spider mite, citrus red mite and European red mite.

Ticks

*Boophilus microplus.*

House dust mites

Acarid mites, Pyroglyphidae, Cheyletidae and *Ornithanyssus bacoti.*

The present compounds are effective especially on spider mites.

Process for production of the present compounds will be explained in detail.

The present compounds can be produced by reacting a halopyrimidine derivative represented by the following formula (II):

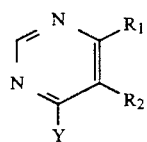

(II)

wherein $R_1$, $R_2$ and Y have the same meanings as above, with an amine derivative represented by the following formula (III):

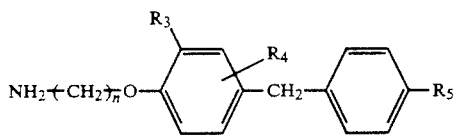

(III)

wherein $R_3$, $R_4$, $R_5$ and n have the same meanings as above, if necessary, in the presence of a base.

Reactron temperature is usually from room temperature to about 250° C., preferably 50° C. to 200° C. and reaction time is about 10 minutes to about 12 hours.

With reference to the amount of the materials used for the reaction, amount of the amine derivative represented by the formula (III) is 1–5 mols, more preferably 1–2 mols based on 1 mol of the halopyrimidine derivative represented by the formula (II) and, if necessary, 1–2 mols of a base can be used. Examples of the base are alkali metal hydroxides such as sodium hydroxide, alkali metal carbonates such as sodium carbonate, organic bases such as triethylamine, N,N-diethylaniline, pyridine, and diazabicycloundecene, and mixtures thereof. When the amine derivative represented by the formula (III) is used in an excess amount in the reaction, this excess amine derivative per se can be used as the base.

In the above reaction, reaction solvent is not necessarily required, but the reaction is generally carried out in the presence of a solvent. The solvent includes, for example, aromatic hydrocarbons such as benzene and toluene, halogenated aromatic hydrocarbons such as chlorobenzene, aliphatic hydrocarbons such as hexane and cyclohexane, halogenated aliphatic hydrocarbons such as chloroform, dichloromethane and dichloroethane, ketones such as acetone, methyl ethyl ketone, and cyclohexanone, esters such as ethyl acetate, ethers such as diethyl ether, tetrahydrofuran, dioxane, and ethylene glycol dimethyl ether, alcohols such as methanol and ethanol, water, N,N-dimethylformamide, pyridine, and mixtures thereof.

After completion of the reaction, the reaction mixture is subjected to usual work-up such as concentration under reduced pressure and extraction and, if necessary, to purification operations such as chromatography and recrystallization, thereby to obtain the desired compound.

Examples of the present compounds which can be produced by the above-mentioned process are shown in Table 1.

TABLE 1

Pyrimidine derivatives represented by the following formula:

| $R_1$ | $R_2$ | n | aryloxy group | $R_5$ |
|---|---|---|---|---|
| $-(CH_2)_3-$ | | 2 | phenoxy (unsubstituted) | H |
| $-(CH_2)_3-$ | | 2 | phenoxy (unsubstituted) | $CH_3$ |
| $-(CH_2)_3-$ | | 2 | phenoxy (unsubstituted) | $SCH_3$ |
| $-(CH_2)_3-$ | | 2 | phenoxy with $CH_3$ | H |
| $-(CH_2)_3-$ | | 2 | phenoxy with $CH_3$ | $CH_3$ |
| $-(CH_2)_3-$ | | 2 | phenoxy with $CH_3$ | $SCH_3$ |
| $-(CH_2)_3-$ | | 2 | phenoxy with $CH_3$, $CH_3$ | H |
| $-(CH_2)_3-$ | | 2 | phenoxy with $CH_3$, $CH_3$ | $CH_3$ |
| $-(CH_2)_3-$ | | 2 | phenoxy with $CH_3$, $CH_3$ | $SCH_3$ |

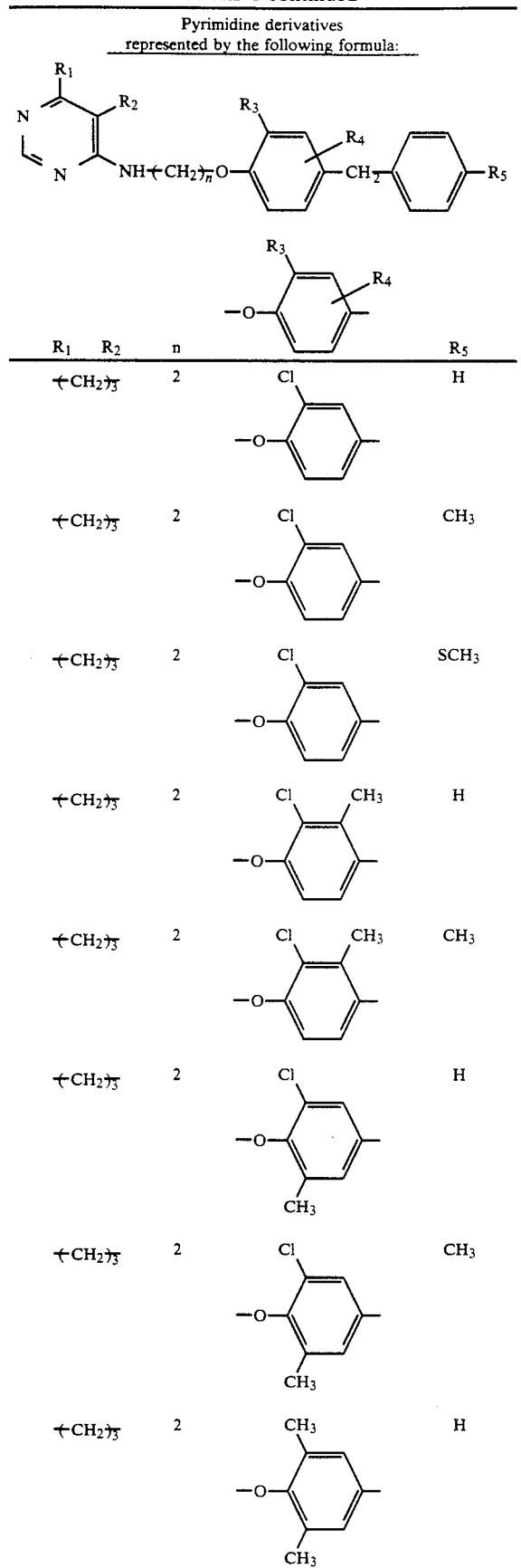
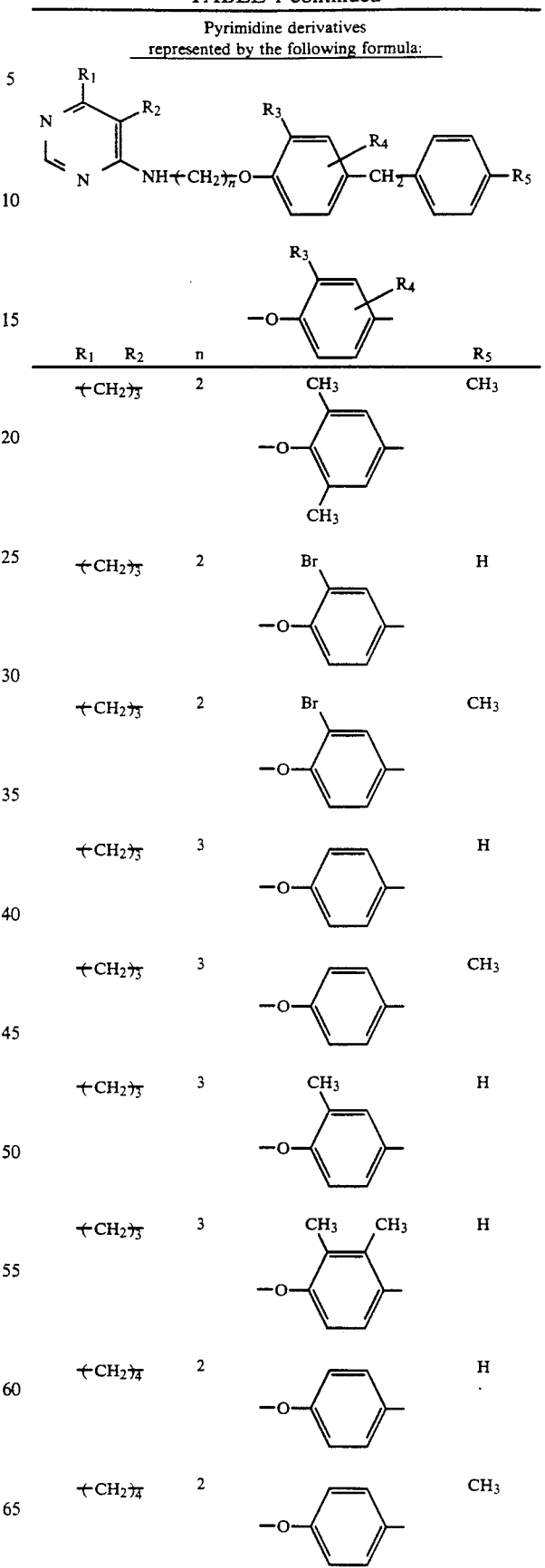

TABLE 1-continued
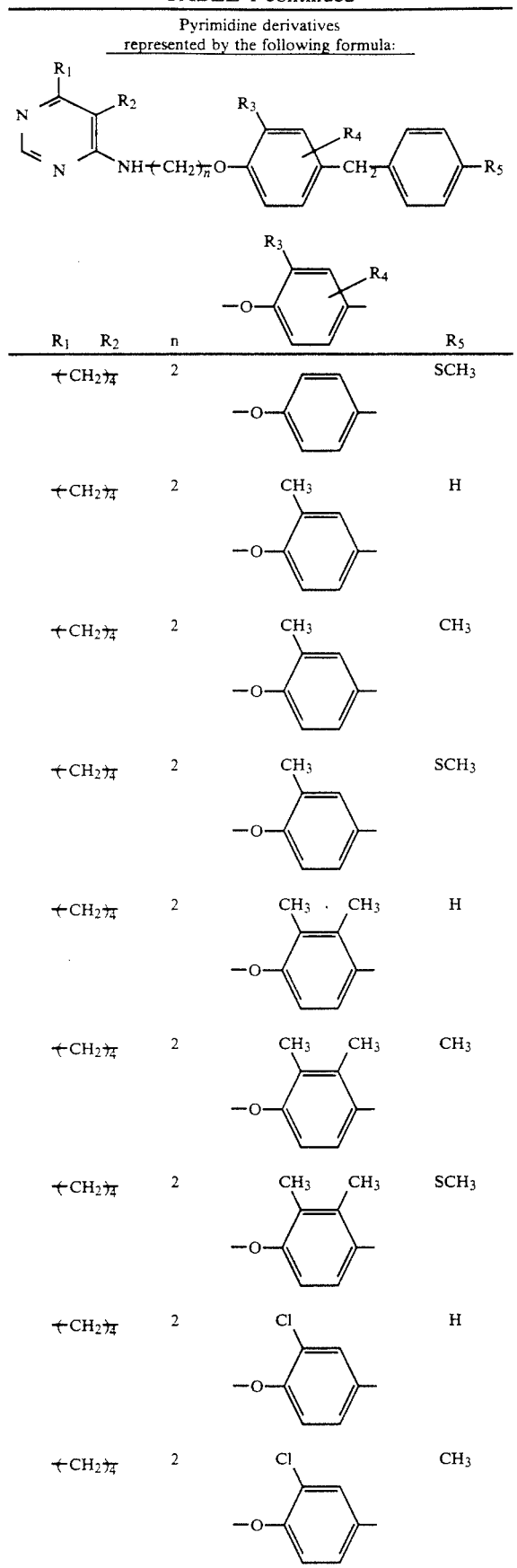
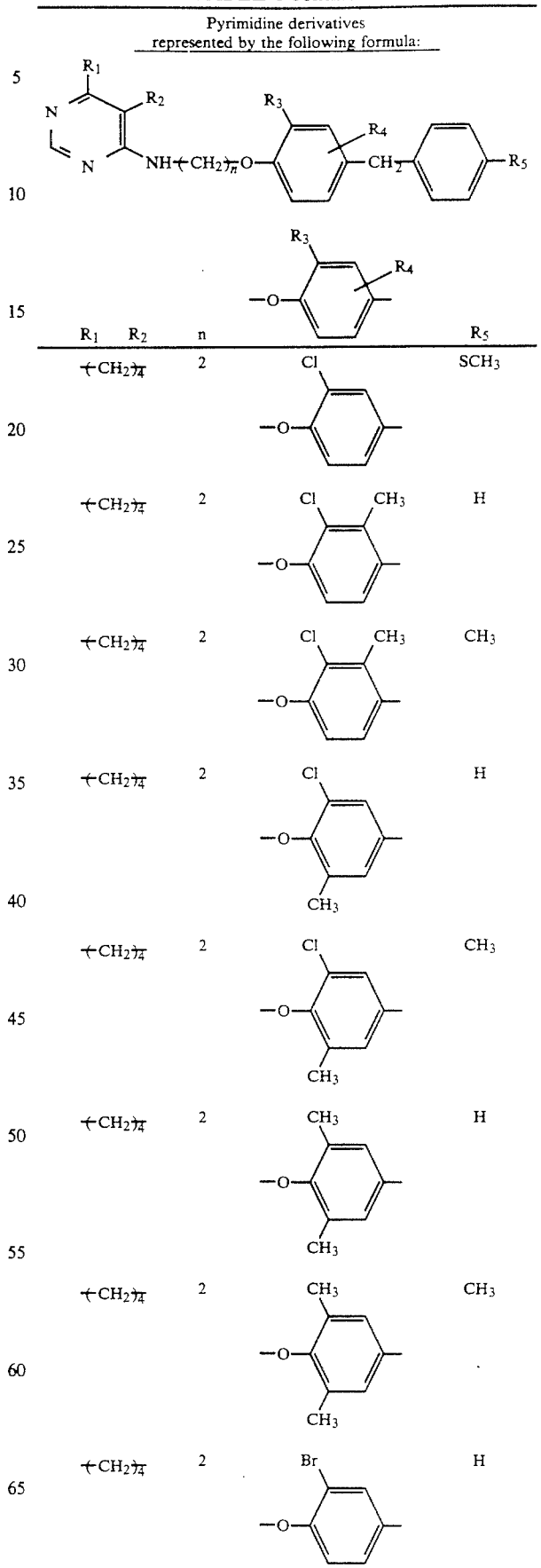

TABLE 1-continued

Pyrimidine derivatives represented by the following formula:

(structure with $R_1, R_2, R_3, R_4, R_5$, $NH\text{-}(CH_2)_n\text{-}O\text{-}$ linkage to aryl-$CH_2$-aryl)

and $-O-$(aryl with $R_3, R_4$)

| $R_1$ $R_2$ | n | (aryl group) | $R_5$ |
|---|---|---|---|
| $-(CH_2)_4-$ | 2 | 3-Br, 4-O- | $CH_3$ |
| $-(CH_2)_4-$ | 2 | 3-Br, 2-CH$_3$, 4-O- | H |
| $-(CH_2)_4-$ | 2 | 3-Br, 5-CH$_3$, 4-O- | $CH_3$ |
| $-(CH_2)_4-$ | 3 | 3-CH$_3$, 4-O- | H |
| $-(CH_2)_4-$ | 3 | 3-CH$_3$, 5-CH$_3$, 4-O- | H |
| $-(CH_2)_4-$ | 3 | 3-Cl, 4-O- | H |
| $-(CH_2)_4-$ | 3 | 3-Br, 4-O- | H |
| $-(CH_2)_4-$ | 3 | 4-O- | H |
| $-(CH_2)_4-$ | 3 | 4-O- | $CH_3$ |
| $-(CH_2)_3-$ | 2 | 3-C$_2$H$_5$, 4-O- | H |
| $-(CH_2)_4-$ | 2 | 3-C$_2$H$_5$, 4-O- | H |

The halopyrimidine derivative represented by the formula (II) which is one starting compound in preparation of the present compounds can be easily prepared by known methods such as the method described in Japanese Patent Kokai Nos. 63-156781 and 58-222070. The amine derivative represented by the formula (III) which is another starting compound in preparation of the present compounds can be prepared, for example, through the following reaction formulas.

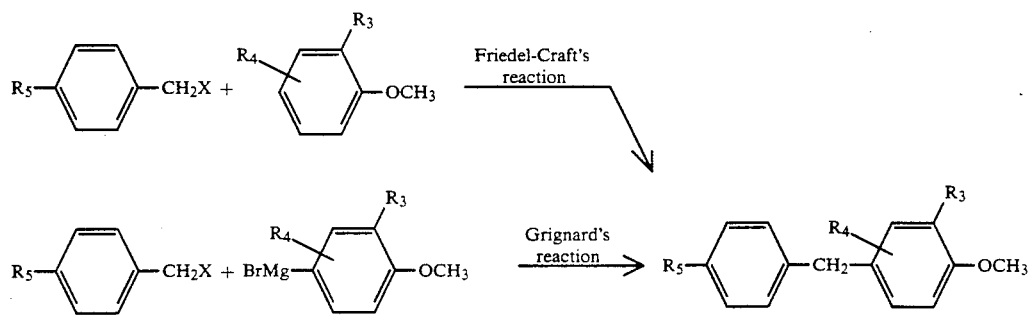

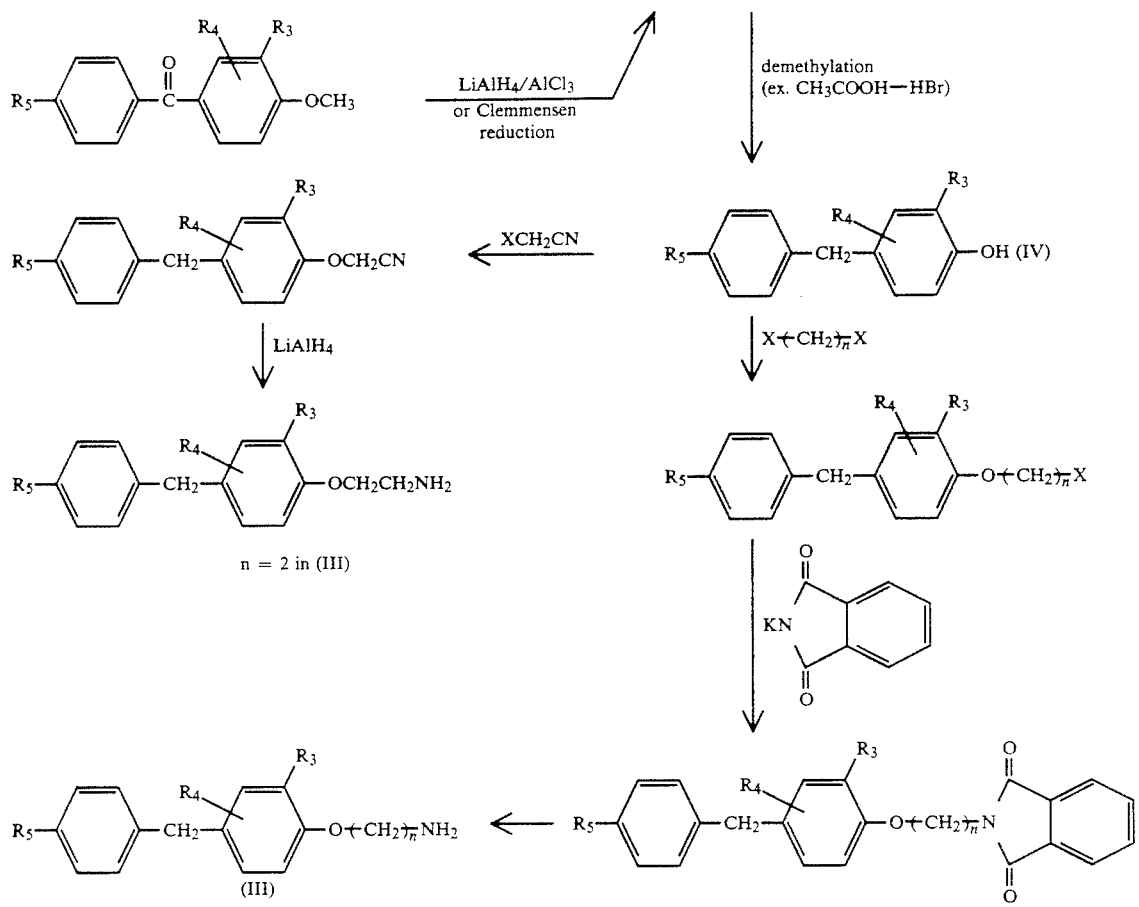

(wherein $R_3$, $R_4$, $R_5$ and n have the same meanings as above and X represents a halogen atom.)

In the above reaction formulas, the phenol derivative represented by the formula (IV) which is an intermediate for preparation of the amine derivative represented by the formula (III) and wherein $R_3$ in the formula (IV) is a chlorine atom can also be prepared by the following reaction formula.

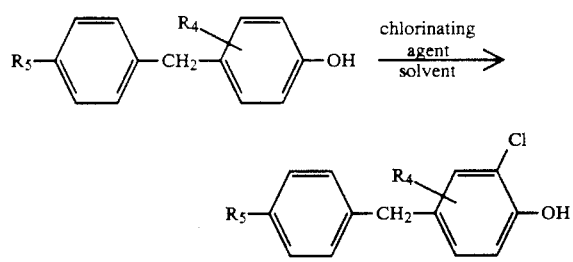

wherein $R_4$ and $R_5$ have the same meanings as above.

When the present compound is used as an active ingredient of fungicides, it may be used without adding any other components, but usually, it is formulated into emulsifiable concentrates, wettable powders, suspension formulations, dusts, granules and the like by mixing with a solid or liquid carrier, a surface active agent and other auxiliaries for formulation. In this case, the content of the present compound as an active ingredient in the formulations is 0.1-99.9 %, preferably 1-90 % by weight.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate and synthetic hydrated silicon dioxide. The liquid carriers include, for example, aromatic hydrocarbons such as xylene and methylnaphthalene, alcohols such as isopropanol, ethylene glycol and cellosolve, ketones such as acetone, cyclohexenone and isophorone, vegetable oils such as soybean oil and cotton seed oil, dimethyl sulfoxide, acetonitrile, and water.

The surface active agents used for emulsification, dispersion, wetting, etc. include, for example, anionic surface active agents such as alkylsulfuric esters, alkylsulfonates, alkylarylsulfonates, dialkylsulfosuccinates, polyoxyethylenealkylaryl ether phosphoric esters, and naphthalenesulfonic acid/formalin condensates and nonionic surface active agents such as polyoxyethylene alkyl ethers, polyoxyethylene polyoxypropylene block copolymer, sorbitan fatty acid esters, and polyoxyethylene sorbitan fatty acid esters. The auxiliaries for formulation include, for example, lignosulfonates, alginates, polyvinyl alcohol, gum arabic, CMC (carboxymethyl cellulose), and PAP (acid isopropyl phosphate).

When the present compound is used as an active ingredient of fungicides, its dosage is usually 0.1-100 g, preferably 0.2-20 g per 1 are. When the present compound is used in the form of emulsifiable concentrate, wettable powder, suspension formulation or the like which is diluted with water, the concentration is 0.0001-0.5 %, preferably 0.0005-0.2 %. Granules and dusts are used as they are without dilution.

The present compound can also be used as a seed disinfectant and besides, can be mixed with other fungicides to enhance fungicidal effect. Furthermore, the present compound can be used in admixture with insecticides, acaricides, nematocides, herbicides, plant growth regulating agents or fertilizers.

When the present compound is used as an active ingredient of acaricides, it is mixed with a solid carrier, a liquid carrier, a gaseous carrier or a bait or is impregnated in base materials for mosquito coils and mats, if necessary, with addition of surface active agents and other auxiliaries for formulation, thereby to formulate into oil sprays, emulsifiable concentrates, wettable powders, flowable concentrates such as water-based suspension formulations and water-based emulsion formulations, granules, dusts, aerosols, heat fumigants such as mosquito coils, electric mosquito mats and electric nonmat formulation, heating smoking agents such as self-burning type smoking agents, chemical reaction type smoking agents and porous ceramic plate-type smoking agents, aerosols such as fogging, ULV agents, poison baits and the like.

These formulations usually contain the present compound in an amount of 0.001-95 % by weight as an active ingredient.

The solid carriers used in formulation include fine powders or granules of, for example, clays (such as kaolin clay, diatomaceous earth, synthetic hydrated silicon dioxide, bentonite, fubasami clay, and acid clay), talcs, ceramics, other inorganic minerals (such as sericite, quartz, sulfur, active carbon, calcium carbonate and hydrated silica) and chemical fertilizers (such as ammonium sulfate, ammonium phosphate, ammonium nitrate, urea, and ammonium chloride). The liquid carriers include, for example, water, alcohols (such as methanol and ethanol), ketones (such as acetone and methyl ethyl ketone), aromatic hydrocarbons (such as benzene, toluene, xylene, ethylbenzene and methylnaphthalene), aliphatic hydrocarbons (such as hexane, cyclohexane, kerosine and light oil). esters (such as ethyl acetate and butyl acetate), nitriles (such as acetonitrile and isobutyronitrile), ethers (such as diisopropyl ether and dioxane), acid amides (such as N,N-dimethylformamide and N,N-dimethylacetamide), halogenated hydrocarbons (such as dichloromethane, trichloroethane and carbon tetrachloride), dimethyl sulfoxide, and vegetable oils (such as soybean oil and cotton seed oil). The gaseous carriers, namely, propellants include, for example, Freon gas ®, butane gas, LPG (liquefied petroleum gas), dimethyl ether, carbon dioxide and the like.

The surface active agents include, for example, alkylsulfuric esters, alkylsulfonates, alkylarylsulfonates, alkylaryl ethers and polyoxyethylated products thereof, polyethylene glycol ethers, polyhydric alcohol esters and sugar alcohol derivatives.

The auxiliaries for formulation such as adhesive agents and dispersants include, for example, casein, gelatin, polysaccharides (such as starch powder, gum arabic, cellulose derivatives and alginic acid), lignin derivatives, bentonite, sugars and synthetic water-soluble polymers (such as polyvinyl alcohol, polyvinyl pyrrolidone and polyacrylic acids). The stabilizers include, for example, PAP (acid isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents and fatty acids or esters thereof.

As base materials for the poison bait, mention may be made of bait components such as grain flour, vegetable oil, sugar and crystalline cellulose, antioxidants such as dibutylhydroxytoluene and nordihydroguaiaretic acid, preservatives such as dehydroacetic acid, erroneous eating inhibitors such as capsicum powder and attractant perfumes such as cheese perfume and onion perfume.

Formulations of flowable concentrates (water-based suspension formulations or water-based emulsion formulations) are generally prepared by finely dispersing 1-75 % of the compound in water containing 0.5-15 % of a dispersing agent, 0.1-10 % of a suspension aid (such as protective colloid or compound which imparts thixotropic properties) and 0-10 % of a suitable auxiliary (such as antifoamer, rust preventive, stabilizer, spreader, penetrating aid, antifreezing agent, antimicrobial agent or mildewproofing agent). It is also possible to prepare oil suspension by using an oil in which the compound is hardly soluble in place of water. As the protective colloid, there may be used, for example, geranine, casein, gums, cellulose ether and polyvinyl alcohol. As the compounds which impart thixotropic properties, there may be used, for example, bentonite, aluminum magnesium silicate, xanthane gum and polyacrylic acid.

The resulting formulations are used as such or diluted with, for example, water. Furthermore, they can be used in admixture with other insecticides, acaricides, fungicides, herbicides, plant growth regulating agents, synergists, fertilizers, soil improvers and the like or they can be used together with these agents without being mixed therewith.

When the present compound is used as an active ingredient of agricultural acaricides, its dosage is usually 0.1-500 g per 10 areas. When the emulsifiable concentrate, wettable powder, flowable concentrates, etc. are diluted with water for use, the concentration is 0.0001-1000 ppm. Granule and dust are used as they are without any dilution. When the present compound is used as an active ingredient of acaricides for disinfestation, the emulsifiable concentrate, wettable powder and flowable concentrate are diluted to 0.0001-10000 ppm with water for use and the oil solution, aerosol, fumigant, smoking agent, fogging agent, ULV agent and poison bait are used as they are.

The dosage and concentration thereof depends on kind of formulation, time, method and place of application, kind of pests and state of diseases and can be increased or decreased regardless of the above-mentioned ranges.

The present invention will be explained in more detail by the following preparation examples, formulation examples and test examples. It should be understood that they should not be construed as limiting the invention.

PREPARATION EXAMPLE 1

A mixture of 1.0 g of 4-chloro-5,6-tetramethylenepyrimidine and 2.67 g of 2-(4-benzylphenoxy)ethylamine was stirred with heating at 150° C. for 1 hour. After the mixture was left for cooling, 50 ml of water was added to the reaction mixture, followed by extracting with 50 ml of chloroform three times. The extract was dried over anhydrous magnesium sulfate and then concentrated under reduced pressure to obtain an oily residue. This was chromatographed on a silica gel column (eluting solvent hexane : acetone=3 : 1 (v/v)) to obtain 0.8 g of 4-[2-(4-benzylphenoxy)ethylamino]-5,6-tetramethylenepyrimidine (the present compound (2)).

PREPARATION EXAMPLE 2

A mixture of 1.0 g of 4-chloro-5,6-tetramethylenepyrimidine and 2.86 g of 2-(4-benzyl-2-methylphenoxy)ethylamine was subjected to reaction and treatment in the same manner as in Preparation Example 1 to obtain 0.75 g of 4-[2-(4-benzyl-2-methylphenoxy)ethylamino]-5,6-tetramethylenepyrimidine (the present compound (8)).

PREPARATION EXAMPLE 3

A mixture of 1.0 g of 4-chloro-5,6-tetramethylenepyrimidine and 3.1 g of 2-(4-benzyl-2-chlorophenoxy)ethylamine was subjected to reaction and treatment in the same manner as in Preparation Example 1 to obtain 1.1 g of 4-[2-(4-benzyl-2-chlorophenoxy)ethylamino]-5,6-tetramethylenepyrimidine (the present compound (3)).

The present compounds which were prepared in accordance with the above preparation examples are shown in Table 2.

TABLE 2

Pyrimidine derivatives represented by the following formula:

| Compound No. | $R_1$ $R_2$ | n | $R_3$, $R_4$ (—O— phenyl with $R_3$, $R_4$) | $R_5$ | Physical properties |
|---|---|---|---|---|---|
| (1) | $+CH_2)_3$ | 2 | —O—⌬— | H | $n_D^{25.5}$ 1.5889 |
| (2) | $+CH_2)_4$ | 2 | —O—⌬— | H | m.p. 113.6° C. |
| (3) | $+CH_2)_4$ | 2 | Cl; —O—⌬— | H | Glassy solid; PMR* 8.34(s, 1H, pyrimidine-H$^2$) |
| (4) | $+CH_2)_4$ | 2 | Br; —O—⌬— | H | Glassy solid; PMR* 8.35(s, 1H, pyrimidine-H$^2$) |
| (5) | $+CH_2)_4$ | 3 | —O—⌬— | H | Glassy solid; PMR* 8.37(s, 1H, pyrimidine-H$^2$) |
| (6) | $+CH_2)_4$ | 2 | —O—⌬— | $CH_3$ | Glassy solid; PMR* 2.29(s, 3H, —CH$_3$) 8.41(s, 1H, pyrimidine-H$^2$) |
| (7) | $+CH_2)_4$ | 2 | —O—⌬— | $SCH_3$ | Glassy solid; PMR* 2.42(s, 3H, —SCH$_3$) 8.35(s, 1H, pyrimidine-H$^2$) |

TABLE 2-continued

Pyrimidine derivatives represented by the following formula:

| Compound No. | $R_1$ | $R_2$ | n | $R_3$ (with ring structure) | $R_5$ | Physical properties |
|---|---|---|---|---|---|---|
| (8) | | $(CH_2)_4$ | 2 | $CH_3$, -O-phenyl | H | m.p. 121.5° C. |
| (9) | | $(CH_2)_4$ | 2 | $CH_3$, $CH_3$, -O-phenyl | H | $n_D^{23.0}$ 1.4719 |
| (10) | | $(CH_2)_4$ | 2 | $CH_3$, -O-phenyl | H | m.p. 108.5° C. |
| (11) | | $(CH_2)_4$ | 2 | $C_2H_5$, -O-phenyl | H | m.p. 136.5° C. |
| (12) | | $(CH_2)_5$ | 2 | $CH_3$, -O-phenyl | H | m.p. 130.0° C. |

*PMR: δ (ppm) value measured using TMS internal standard in CDCl$_3$

Preparation examples of the starting compounds used for preparation of the present compounds are shown below.

REFERENCE EXAMPLE 1

Preparation of 2-(4-benzylphenoxy)ethylamine (a) 18.4 g of 4-benzylphenol was dissolved in 100 ml of anhydrous tetrahydrofuran and 4.0 g of sodium hydride (60 % oil dispersion) was gradually added to the solution with ice cooling :n nitrogen stream. The solution was stirred for 1 hour at room temperature and 12.0 g of bromoacetonitrile was added thereto under ice cooling, followed by refluxing with heating for 3 hours. After being left for cooling, the reaction mixture was concentrated under reduced pressure and to the residue was added 100 ml of water, followed by extracting twice with 100 ml of chloroform. The extract was washed with water, dried over anhydrous magnesium sulfate and concentrated under reduced pressure to obtain an oily residue. The residue was chromatographed on a silica gel column (eluting solvent hexane : acetone = 3 : 1 (v/v)) to obtain 19.1 g of (4-benzylphenoxy)acetonitrile.

(b) 3.4 g of lithium aluminum hydride was suspended in 100 ml of anhydrous tetrahydrofuran and to the suspension was gradually added 10.0 g of (4-benzylphenoxy)acetonitrile under ice cooling in nitrogen stream. After stirring at room temperature for 1 hour and ice cooling, to the reaction mixture were carefully added 3.4 ml of water, then 3.4 ml of 5N aqueous sodium hydroxide solution and finally 10 ml of water, followed by stirring for a while. Undesired matters were removed by filtration with cerite and the filtrate was concentrated under reduced pressure to obtain 9.8 g of 2-(4-benzylphenoxy)ethylamine. This was used for the subsequent reaction without further purification.

REFERENCE EXAMPLE 2

Preparation of 2-(4-benzyl-2-methylphenoxy)ethylamine (a) Grignard reagent was prepared from 12.15 g of magnesium (turnings) and 50.23 g of 1-bromo-4- methoxy-3-methylbenzene in 200 ml of anhydrous ether by conventional process. To this Grignard reagent was added 200 ml of anhydrous benzene and ether was distilled off under normal pressure. To this solution was added dropwise a mixed solution comprising 47.25 g of benzyl chloride and 50 ml of anhydrous benzene under refluxing with heating, followed by stirring for 3 hours. After being left for cooling, the reaction mixture was filtered and the filtrate was washed with dilute hydrochloric acid, dilute aqueous sodium hydroxide solution and water in this order. The filtrate was dried over anhydrous magnesium sulfate and then was concentrated under reduced pressure and thereafter, distilled under reduced pressure to obtain 30.8 g of 4-benzyl-2-methyl-1-methoxybenzene.

(b) A mixture of 30.8 g of 4-benzyl-2-methyl-1-methoxybenzene with 50 ml of hydrobromic acid and 100 ml of acetic acid was refluxed with heating for 5 hours. This was left for cooling and neutralized with an aqueous sodium hydrogen-carbonate solution and was extracted twice with 100 ml of ethyl acetate. The extract was dried over anhydrous magnesium sulfate and then was concentrated under reduced pressure. The resulting oily residue was chromatographed on a silica gel column (eluting solvent hexane : acetone=3 : 1 (v/v)) to obtain 23.7 g of 4-benzyl-2-methylphenol.

(c) 2-(4-benzyl-2-methylphenoxy)ethylamine was prepared from 4-benzyl-2-methylphenol in the same manner as in Reference Example 1.

REFERENCE EXAMPLE 3

Preparation of 2-(4-benzyl-2-chlorophenoxy)ethylamine (a) 18.4 g of 4-benzylphenol was dissolved in 100 ml of carbon tetrachloride and thereto was added dropwise 10.85 g of t-butyl hypochlorite at $-5°-0°$ C. with stirring. After stirring for 3 hours at room temperature, the reaction mixture was washed with a saturated aqueous sodium hydrogen-carbonate solution and then with water, then dried over anhydrous magnesium sulfate and thereafter, concentrated under reduced pressure. The resulting oily residue was chromatographed on a silica gel column (eluting solvent hexane : acetone=3 : 1 (v/v)) to obtain 20.6 g of 4-benzyl-2-chlorophenol.

(b) 2-(4-benzyl-2-chlorophenoxy)ethylamine was prepared from 4-benzyl-2-chlorophenol in the same manner as in Reference Example 1.

Next, formulation examples will be shown below, where part is by weight.

FORMULATION EXAMPLE 1

50 parts of each of the present compounds (1)–(12), 3 parts of calcium lignosulfonate, 2 parts of sodium laurylsulfate and 45 parts of synthetic hydrated silicon dioxide are thoroughly pulverized and mixed to obtain a wettable powder.

FORMULATION EXAMPLE 2

25 parts of each of the present compounds (1)–(12), 3 parts of polyoxyethylenesorbitan monooleate, 3 parts of CMC and 69 parts of water are mixed and wet-pulverized until the particle size of the active ingredient reaches not more than 5 microns to obtain a suspension formulation.

FORMULATION EXAMPLE 3

2 parts of each of the present compounds (1)–(12), 88 parts of kaolin clay and 10 parts of talc are thoroughly pulverized and mixed to obtain a dust.

FORMULATION EXAMPLE 4

20 parts of each of the present compounds (1)–(12), 14 parts of polyoxyethylene styrylphenyl ether, 6 parts of calcium dodecylbenzenesulfonate and 60 parts of xylene are thoroughly mixed to obtain an emulsifiable concentrate.

FORMULATION EXAMPLE 5

2 parts of each of the present compounds (1)–(12), 1 part of synthetic hydrated silicon dioxide, 2 parts of calcium lignosulfonate, 30 parts of bentonite and 65 parts of kaolin clay are thoroughly pulverized and mixed, well kneaded with water, then granulated and dried to obtain a granule.

FORMULATION EXAMPLE 6

10 parts of each of the present compounds (1)–(12) is dissolved in 35 parts of xylene and 35 parts of dimethylformamide and to the solution are added 14 parts of polyoxyethylene styrylphenyl ether and 6 parts of calcium dodecylbenzenesulfonate, followed by well stirring and mixing to obtain an emulsifiable concentrate of 10 % in concentration.

FORMULATION EXAMPLE 7

0.1 part of each of the present compounds (1)–(12) is dissolved in 5 parts of xylene and 5 parts of trichloroethane and the solution is mixed with 89.9 parts of deodorized kerosine to obtain an oil spray of 0.1 % in concentration.

FORMULATION EXAMPLE 8

0.1 part of each of the present compounds (1)–(12), 0.2 part of tetramethrin, 0.1 part of d-phenothrin, 10 parts of trichloroethane and 59.6 parts of deodorized kerosene are mixed and dissolved. The solution is filled in an aerosol container, to which a valve portion is fitted. Then, 30 parts of a propellant (liquefied petroleum gas) is filled under pressure in the container through the valve portion to obtain an oil-based aerosol.

The following test examples demonstrate the effectiveness of the present compound as fungicides, insecticides and/or acaricides. The present compounds used in the test examples are identified by the compound numbers shown in Table 2 and the compounds used for comparison are identified by the compound symbols shown in Table 3.

TABLE 3

| Compound symbol | Structural formula | Notes |
| --- | --- | --- |
| (A) | [pyrimidine with C2H5, C2H5, NHCH2CH2O-phenyl(CH3)(CH3)] | Compound mentioned in Japanese Patent Kokai No. 63-156781 |
| (B) | [quinazoline with NHCH2CH2O-phenyl-CH2-phenyl] | Compound mentioned in Japanese Patent Kokai No. 55-76804 |
| (C) | [pyrimidine with C2H5, Cl, NHCH2CH2O-phenyl-CH2-phenyl] | Compound mentioned in EP-A-453137 |
| (D) | [pyrimidine with C2H5, Cl, NHCH2CH2O-(Cl-phenyl)-CH2-phenyl] | Compound mentioned in EP-A-453137 |
| (E) | [pyrimidine with C2H5, Cl, NHCH2CH2O-(CH3-phenyl)-CH2-phenyl] | Compound mentioned in EP-A-453137 |

First, the effectiveness of the present compounds as fungicides is shown by the following test examples.

The controlling effect was evaluated by visually observing the state of disease of the test plants, namely, degree of fungus colony and infected area on the leaves and stems of the test plants. The results of evaluation were expressed in terms of six ratings as follows:

"5" Not observed at all.
"4" Observed on about 10 % of the leaves and stems.
"3" Observed on about 30 % of the leaves and stems.
"2" Observed on about 50 % of the leaves and stems.
"1" Observed on about 70 % of the leaves and stems.
"0" Same as when no compound was used.

TEST EXAMPLE 1

Test for controlling effect on Phytophthora infestans of tomato (preventive controlling effect)

Tomato (Ponte rosa) seeds were sown in the sandy loam filled in a plastic pot. After raising for 20 days in a greenhouse, the seedlings with two foliage leaves were subjected to foliage application with a spray liquid of the wettable powder prepared according to Formulation Example 1 which was diluted with water to a given concentration so that the liquid was sufficiently applied to the surface of the leaves. After application, the seedlings were inoculated with zoospores of Phytophthora infestans of tomato by spraying a suspension containing the zoospores. The inoculated seedlings were kept at 23° C. in a damp place overnight and were further grown for 4 days in a greenhouse. The controlling effect was examined. The results are shown in Table 4.

TABLE 4

| Test compounds | Concentration of active ingredient (ppm) | Controlling effect |
| --- | --- | --- |
| (1) | 50 | 5 |
|  | 12.5 | 4 |
| (2) | 50 | 5 |
|  | 12.5 | 5 |
| (3) | 50 | 5 |
|  | 12.5 | 5 |
| (4) | 50 | 5 |
|  | 12.5 | 5 |
| (5) | 50 | 5 |
|  | 12.5 | 4 |
| (8) | 50 | 5 |
|  | 12.5 | 5 |
| (10) | 50 | 5 |
|  | 12.5 | 4 |
| (11) | 50 | 5 |
|  | 12.5 | 4 |
| (12) | 50 | 5 |
|  | 12.5 | 5 |
| (A) | 50 | 3 |
|  | 12.5 | 1 |
| (B) | 50 | 3 |

TABLE 4-continued

| Test compounds | Concentration of active ingredient (ppm) | Controlling effect |
|---|---|---|
| | 12.5 | 3 |

TEST EXAMPLE 2

Test for controlling effect on *Phytophthora infestans* of tomato (preventive controlling effect)

Tomato (*Ponte rosa*) seeds were sown in the sandy loam filled in a plastic pot. After raising for 20 days in a greenhouse, the seedlings with two foliage leaves were subjected to foliage application with a spray liquid of the wettable powder prepared according to Formulation Example 1 which was diluted with water to a given concentration so that the liquid was sufficiently applied to the surface of the leaves. After one day of the application, the seedlings were inoculated with zoospores of Phytophthora infestans of tomato by spraying a suspension containing the zoospores. The inoculated seedlings were kept at 23° C. in a damp place overnight and were further grown for 4 days in a greenhouse. The controlling effect was examined. The results are shown in Table 5.

TABLE 5

| Test Compounds | Controlling effect | | |
|---|---|---|---|
| | 200 | 50 | 12.5 (ppm) |
| (2) | 5 | 5 | 4 |
| (3) | 5 | 4 | 4 |
| (8) | 5 | 5 | 5 |
| (C) | 4 | 3 | 3 |
| (D) | 4 | 3 | 2 |
| (E) | 5* | 5 | 5 |

*Phytotoxicity, i.e., growth inhibition of plants was observed.

TEST EXAMPLE 3

Test for controlling effect on *Plasmopara viticola* of grapevine (preventive controlling effect)

Grapevine (Berry A) seeds were sown in the sandy loam filled in a plastic pot. After raising for 40 days in a greenhouse, the seedlings with three foliage leaves open were subjected to foliage application with a spray liquid of the suspension formulation prepared according to Formulation Example 2 which was diluted with water to a given concentration so that the liquid was sufficiently applied to the surface of the leaves. After application, the seedlings were inoculated with zoospores of Plasmopara viticola by spraying a suspension containing the zoospores. The inoculated seedlings were kept at 23° C. in a damp place overnight and were further grown for 7 days in a greenhouse. The controlling effect was examined. The results are shown in Table 6.

TABLE 6

| Test compounds | Concentration of active ingredient (ppm) | Controlling effect |
|---|---|---|
| (1) | 200 | 5 |
| (2) | 200 | 5 |
| (3) | 200 | 5 |
| | 50 | 5 |
| (4) | 200 | 5 |
| (6) | 200 | 5 |
| (8) | 200 | 5 |
| | 50 | 5 |
| | 12.5 | 4 |
| (10) | 200 | 5 |

TABLE 6-continued

| Test compounds | Concentration of active ingredient (ppm) | Controlling effect |
|---|---|---|
| (11) | 200 | 5 |
| (12) | 200 | 5 |
| (A) | 200 | 2 |
| (B) | 200 | 2 |

TEST EXAMPLE 4

Test for controlling effect on *Phytophthora infestans* of tomato (curative effect)

Tomato (*Ponte rosa*) seeds were sown in the sandy loam filled in a plastic pot. After raising for 20 days in a greenhouse, the seedlings with two leaves open were inoculated with zoospores of Phytophthora infestans of tomato by spraying a suspension of the spores. The inoculated seedlings were kept at 23° C. in a damp place overnight. The seedlings were subjected to foliage application with a spray liquid of the emulsion prepared according to Formulation Example 2 which was diluted to the given concentrations so that sufficient liquid was deposited on the leaves. After application, the seedlings were further grown for 4 days in a greenhouse, and the controlling effect was examined. The results are shown in Table 7.

TABLE 7

| Test compounds | Concentration of active ingredient (ppm) | Controlling effect |
|---|---|---|
| (1) | 200 | 5 |
| (2) | 200 | 5 |
| | 50 | 5 |
| (3) | 200 | 5 |
| | 50 | 4 |
| (4) | 200 | 5 |
| (6) | 200 | 5 |
| | 50 | 5 |
| (8) | 200 | 5 |
| | 50 | 5 |
| (9) | 200 | 5 |
| | 50 | 4 |
| (A) | 200 | 0 |
| (B) | 200 | 0 |

TEST EXAMPLE 5

Test for controlling effect on *Phytophthora infestans* of tomato (curative effect)

Tomato (*Ponte rosa*) seeds were sown in the sandy loam filled in a plastic pot. After raising for 20 days in a greenhouse, the seedlings with two leaves open were inoculated with zoospores of Phytophthora infestans of tomato by spraying a suspension of the spores. The inoculated seedlings were kept at 23° C. in a damp place overnight. The seedlings were subjected to foliage application with a spray liquid of the emulsion prepared according to Formulation Example 2 which was diluted to the given concentrations so that sufficient liquid was deposited on the leaves. After application, the seedlings were further grown for 5 days in a greenhouse, and the controlling effect was examined. The results are shown in Table 8.

TABLE 8

| Test compounds | Controlling effect | | |
|---|---|---|---|
| | 200 | 50 | 12.5 (ppm) |
| (2) | 5 | 4 | 3 |
| (3) | 4 | 3 | 2 |

| Test      | Controlling effect |    |           |
|-----------|--------------------|----|-----------|
| compounds | 200                | 50 | 12.5 (ppm)|
| (8)       | 5                  | 4  | 3         |
| (C)       | 3                  | 1  | 0         |
| (D)       | 1                  | 0  | 0         |
| (E)       | 4                  | 3  | 1         |

TABLE 8-continued

Next, that the present compounds are useful as active ingredient of acaricides is shown by the following test examples.

TEST EXAMPLE 6 (ACARICIDAL TEST ON CARMINE SPIDER MITE)

Ten female images of carmine spider mites per one leaf were parasitized on a potted *Phaseolus vulgaris* (the first leaf) 7 days after sowing and this pot was placed in a thermostatic chamber of 25° C. After 6 days, the plant was sprayed with a liquid prepared by diluting the emulsifiable concentrate prepared according to Formulation Example 6 to a concentration of active ingredient of 500 ppm in an amount of 15 ml per one pot on a turning table and simultaneously 2 ml of the liquid was soil-injected. After 8 days, damage of the plants caused by carmine spider mite was evaluated. Criteria for evaluation of the effect were as follows.

−: Substantially no damage was recognized.
+: A slight damage was recognized.
++: The similar damage to the damage in the untreated section was recognized.

The results are shown in Table 9.

TABLE 9

| Test compounds | Results |
|----------------|---------|
| (1)            | —       |
| (2)            | —       |
| (3)            | —       |
| (4)            | —       |
| (5)            | —       |
| (6)            | —       |
| (7)            | —       |
| (8)            | —       |
| (9)            | —       |
| (10)           | —       |
| (11)           | —       |
| (12)           | —       |

TEST EXAMPLE 7

(Acaricidal test on twospotted spider mites)

Each of the emulsifiable concentrates obtained according to Formulation Example 6 was diluted with water to a given concentration. 40 ml of this diluted liquid was sprayed onto two potted *Paseolus vulgaris* parasitized with twospotted spider mites and simultaneously the diluted liquid was soilinjected in an amount of 2 ml per one pot. The number of female images before the treatment, and after 11 days and 15 days from the treatment was counted and controlling value was obtained by the following formula.

$$\text{Controlling value (\%)} = \left(1 - \frac{C_0^*(T_{11} + T_{15})}{T_0^{**}(C_{11} + C_{15})}\right) \times 100$$

*$C_0$, $C_{11}$ and $C_{15}$ mean the numbers of female imagos in untreated section before treatment and after 11 days and 15 days, respectively.
**$T_0$, $T_{11}$ and $T_{15}$ mean the numbers of female imagos in treated section before treatment and after 11 days and 15 days, respectively.

The results are shown in Table 10.

TABLE 10

| Test compounds | Concentration of active ingredient (ppm) | Controlling value |
|----------------|------------------------------------------|-------------------|
| (1)            | 100                                      | 95                |
|                | 50                                       | 63                |
| (6)            | 100                                      | 95                |
|                | 50                                       | 70                |
| (8)            | 100                                      | 100               |
|                | 50                                       | 100               |
| (A)            | 50                                       | 22                |
| (B)            | 50                                       | 10                |

We claim:

1. A compound represented by the formula:

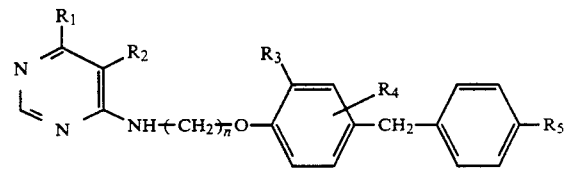

wherein $R_1$ and $R_2$ are bonded together at their termini and represent trimethylene or tetramethylene, $R_3$ represents a hydrogen atom, a lower alkyl group or a halogen atom, $R_4$ represents a hydrogen atom or a lower alkyl group, $R_5$ represents a hydrogen atom, a lower alkyl group or a methylthio group, and n represents 2 or 3.

2. A compound according to claim 1, wherein n represents 2.

3. A compound according to claim 1 or 2 wherein $R_1$ and $R_2$ are bonded together at their termini and represent tetramethylene.

4. A compound according to claim 1 or 2, wherein each of $R_3$, $R_4$ and $R_5$ represents hydrogen; or each of $R_3$ and $R_4$ represents hydrogen, and $R_5$ represents methyl or methylthio; or $R_3$ represents methyl, and each of $R_4$ and $R_5$ represents hydrogen; or each of $R_3$ and $R_4$ represents methyl, and $R_5$ represents hydrogen or methyl.

5. A compound according to claim 1 or 2, wherein $R_3$ represents methyl, and each of $R_4$ and $R_5$ represents hydrogen; or each of $R_3$ and $R_4$ represents methyl, and $R_5$ represents hydrogen or methyl.

6. A compound of the formula

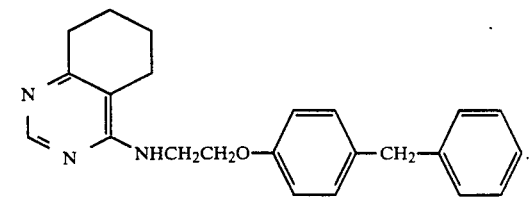

7. A compound of the formula

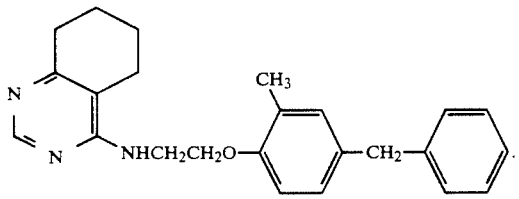

8. A compound of the formula

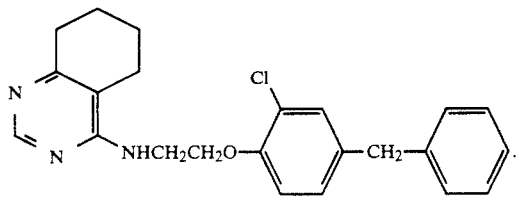

9. A fungicidal composition which comprises as an active ingredient a fungicidally effective amount of a compound according to claim 1.

10. An acaricidal composition which comprises as an active ingredient an acaricidally effective amount of a compound according to claim 1.

11. A method for controlling acarines which comprises applying an acaricidally effective amount of a compound according to claim 1 to the acarines.

12. A method for controlling plant diseases which comprises applying a fungicidally effective amount of a compound according to claim 1 to the plants.

13. A compound according to claim 3, wherein each of $R_3$, $R_4$ and $R_5$ represents hydrogen; or each of $R_3$ and $R_4$ represents hydrogen, and $R_5$ represents methyl or methylthio; or $R_3$ represents methyl, and each of $R_4$ and $R_5$ represents hydrogen; or each of $R_3$ and $R_4$ represents methyl, and $R_5$ represents hydrogen or methyl.

14. A compound according to claim 3, wherein $R_3$ represents methyl, and each of $R_4$ and $R_5$ represents hydrogen; or each of $R_3$ and $R_4$ represents methyl, and $R_5$ represents hydrogen or methyl.

* * * * *